United States Patent
Korkeamäki

(10) Patent No.: US 11,446,422 B2
(45) Date of Patent: Sep. 20, 2022

(54) COLLECTION LINER

(71) Applicant: Serres Oy, Kauhajoki AS (FI)

(72) Inventor: Rami-Matti Korkeamäki, Kauhajoki AS (FI)

(73) Assignee: Serres Oy, Kauhajoki AS (FI)

(*) Notice: Subject to any disclaimer, the term of this patent is extended or adjusted under 35 U.S.C. 154(b) by 0 days.

(21) Appl. No.: 16/965,830

(22) PCT Filed: Feb. 21, 2019

(86) PCT No.: PCT/FI2019/050137
§ 371 (c)(1),
(2) Date: Jul. 29, 2020

(87) PCT Pub. No.: WO2019/162572
PCT Pub. Date: Aug. 29, 2019

(65) Prior Publication Data
US 2021/0052787 A1 Feb. 25, 2021

(30) Foreign Application Priority Data

Feb. 22, 2018 (FI) ........................................ 20185164

(51) Int. Cl.
*A61M 1/00* (2006.01)
(52) U.S. Cl.
CPC ............ *A61M 1/604* (2021.05); *A61M 1/784* (2021.05); *A61M 2209/08* (2013.01)
(58) Field of Classification Search
CPC ...... A61M 1/604; A61M 1/62; A61M 1/0011; B65D 33/007; B65D 33/16; B65D 35/00; B31B 70/26; B31B 70/261; B31B 70/262
See application file for complete search history.

(56) References Cited

U.S. PATENT DOCUMENTS

| | | | |
|---|---|---|---|
| 3,993,222 A | * | 11/1976 | Briggs ...................... A61J 1/05 222/107 |
| 2008/0061064 A1 | * | 3/2008 | Michaels .............. A61M 1/604 220/495.06 |

(Continued)

FOREIGN PATENT DOCUMENTS

| | | |
|---|---|---|
| EP | 1 736 183 A1 | 12/2006 |
| GB | 2 333 459 A | 7/1999 |

(Continued)

OTHER PUBLICATIONS

International Search Report received for PCT Application Serial No. PCT/FI2019/050137 dated May 31, 2019, 10 pages.

(Continued)

*Primary Examiner* — Tatyana Zalukaeva
*Assistant Examiner* — Meagan Ngo
(74) *Attorney, Agent, or Firm* — FisherBroyles, LLP

(57) ABSTRACT

A collection liner for a medical or a surgical operation includes a closed flexible bag portion. The closed flexible bag portion has a width direction (W) and a length direction (L). The closed flexible bag portion includes an upper part of the bag portion in the length direction and a lower part of the bag portion in the length direction. The lower part of the bag portion is folded inside the upper part of the bag portion in such a manner that the entire lower volume of the lower part is upside down inside the upper part.

6 Claims, 8 Drawing Sheets

(56) References Cited

U.S. PATENT DOCUMENTS

| | | | | |
|---|---|---|---|---|
| 2009/0036847 A1* | 2/2009 | Rajamaki | ............... | A61M 1/882 |
| | | | | 604/319 |
| 2009/0292263 A1* | 11/2009 | Hudspeth | ............ | A61M 1/0001 |
| | | | | 604/313 |
| 2011/0198353 A1* | 8/2011 | Tsao | ......................... | A61M 1/63 |
| | | | | 220/495.06 |
| 2013/0343676 A1* | 12/2013 | Dais | ................. | B65D 33/25865 |
| | | | | 383/33 |

FOREIGN PATENT DOCUMENTS

| | | |
|---|---|---|
| JP | H11-130091 A | 5/1999 |
| JP | 2009-526556 A | 7/2009 |
| JP | 2012-24951 A | 2/2012 |
| JP | 2015-024085 A | 2/2015 |
| JP | 2015-024086 A | 2/2015 |
| WO | 2007/093670 A1 | 8/2007 |
| WO | 2013/054824 A1 | 4/2013 |
| WO | 2018/007685 A1 | 1/2018 |
| WO | 2019/162572 A1 | 8/2019 |

OTHER PUBLICATIONS

Finnish Search Report received for Finnish Applicatin Serial No. 20185164 dated Sep. 12, 2018, 1 page.
Notice of Reasons for Refusal received for Japanese Patent Application Serial No. 2020-543925 dated Oct. 12, 2021, 7 pages. (Including English Translation).

* cited by examiner

COLLECTION LINER

CROSS-REFERENCE TO RELATED APPLICATIONS

This application is a National Stage application of International Application No. PCT/FI2019/050137, filed Feb. 21, 2019, which claims benefit to Finnish Application No. 20185164, filed Feb. 22, 2018, which are incorporated by reference herein in their entireties.

FIELD

The present invention relates to a collection liner for a medical or surgical operation. The collection liner comprises a closed flexible bag portion. The closed flexible bag portion has a width direction and a length direction. The bag portion also comprises an upper part of the bag portion in the length direction and a lower part of the bag portion in the length direction.

BACKGROUND

Collection liners are used during a medical or a surgical operation. It is crucial in such operations that no malfunctions occur. The collection liners shall take in the predetermined volume of fluid. It may be jeopardized by collapsed portions of the collection liner which exist when the collection liner has not opened properly inside a collection canister. Further, it is possible that vacuum starts to stretch some part of the incompletely opened flexible collection liner in such a manner that the liner eventually breaks.

Another problem is that the collection liner is strenuous to be fitted in the collection canister because they are about the same size. This may slow down the process of changing the collection liner.

SUMMARY

An object of the present invention is to provide a collection liner so as to overcome the above problems. The objects of the invention are achieved by a collection liner which is characterized by what is stated in the independent claim. The preferred embodiments of the invention are disclosed in the dependent claims.

An advantage of the collection liner of the invention is that it can be assembled into the collection canister easily and reliably. One has not have to adjust the bag portion manually but the bag portion places itself inside the canister in an advantageous manner.

The collection liner comprises a closed flexible bag portion. The flexible bag portion is closed by a closing device. The bag portion may be closed, for example, by a lid, or a handle. The closing device, such as the lid or the handle, comprises all necessary inlets, such as an inlet for vacuum, an inlet for a collection tube, or an inlet for other substances like solidifying agent. Thus, any entrance to the closed bag portion may pass through the closing device.

The closed flexible bag portion is made of flexible plastic film whose thickness is substantially the same throughout the bag portion. The closed flexible bag portion has a width direction and a length direction. The closed flexible bag portion has a first edge in the width direction and a second edge in the width direction. The width of the bag portion is typically substantially constant throughout the length direction of the bag portion, a possible exception is at the bottom seam of the bag portion because the bottom seam may be arched. Between the first edge and the second edge the bag portion is substantially flat when the bag portion is empty.

In the length direction the closed flexible bag portion has an upper part of the bag portion and a lower part of the bag portion. The lower bag portion comprises a lower volume. The lower volume refers to the space of the lower bag portion which is capable of receiving fluid. Besides the lower volume the lower part of the bag portion may comprise e.g. a bottom portion comprising an ancillary handle. The lower part of the bag portion is folded inside the upper part of the bag portion in such a manner that the entire lower volume of the lower part is upside down inside the upper part. Further, the collection liner may also be folded in the width direction in such a manner that the first edge and the second edge are attached together by a joining strip. The joining strip may be an adhesive label, or another suitable fastening means.

When the collection liner is taken into use the flexible bag portion is placed inside a collection canister, i.e. the collection liner is set inside the collection canister. If the collection liner is provided with the lid, the lid closes the open end of the canister. If the collection liner is provided with the handle, the handle is placed between the body of the canister and the lid of the canister in such a manner that the inlet for the collection tube extends from between the body of the canister and the lid.

The opening of the collection liner is assisted by a pressure difference between the collection canister and the collection liner. As the collection canister is evacuated and air is led to the collection liner, the collection liner starts to inflate, and the joining strip, if it exists, breaks. Thus, the upper part of the bag portion meets the inner wall of the canister. The lower part of the bag portion, which is folded inside the upper part of the bag portion, starts to roll out towards the bottom of the canister. Because the collection liner rolls out the bag portion does not rub the side wall of the canister. In addition to the above-mentioned fact, the opposite sides of the inflated collection liner cannot rub each other. This minimize the force required for the liner opening. Thus, the bag portion does not stick to the side wall of the canister, or to itself. This is important because a bag portion that is stuck to the side wall of the canister or to itself may comprise collapsed portions and thus, the bag portion may take in less fluid than assumed. This may lead to the malfunction of the fluid collecting system.

BRIEF DESCRIPTION OF THE DRAWINGS

In the following the invention will be described in greater detail by means of preferred embodiments with reference to the attached drawings, in which.

DETAILED DESCRIPTION

Collection liners 3 and 21, which are shown in FIGS. 1 to 8, are examples of collection liners which are usable in connection with the present invention.

Figure 1:
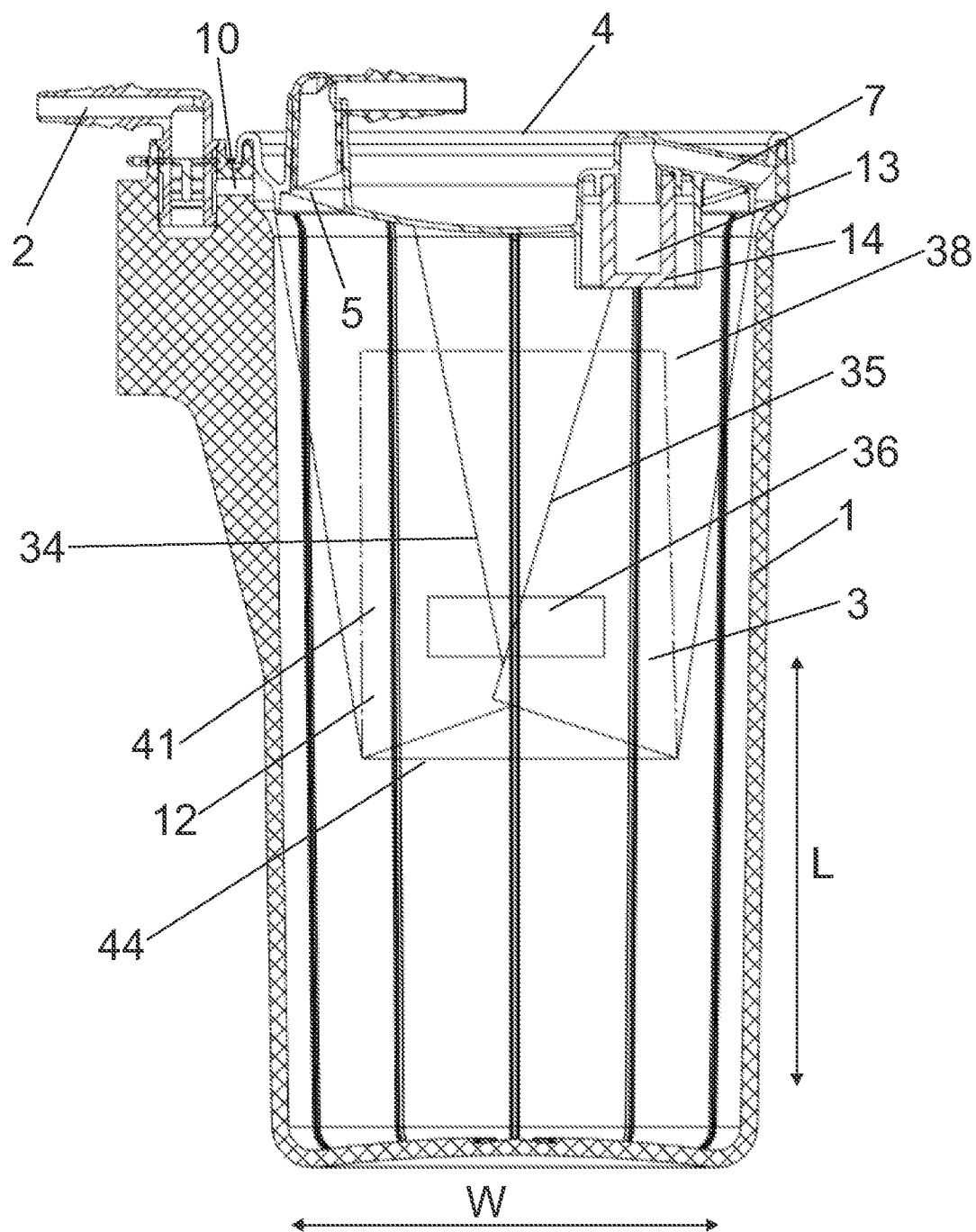
FIG. 1 shows a cross-sectional view of a folded collection liner with a lid inside a collection canister.

FIG. 1 shows a cross-sectional view of a collection liner 3 with a lid 4 inside a collection canister 1. Letter L denotes the length direction of the collection liner and letter W denotes the width direction of the collection liner 3.

The collection canister 1 is open at one end. The collection liner 3 that may be arranged to the collection canister 1 and comprises a flexible bag portion 12 is fixedly fastened to a lid 4. The lid 4 may be a uniform piece. The lid 4 is provided with an inlet for a collection tube 5 which brings fluid from a surgical or medical site.

The collection canister 1 is provided with a vacuum port 2, which is in a flow connection with a source of negative pressure. Vacuum causes suction through an inlet for vacuum 13. The inlet for vacuum 13 is connected to the vacuum port 2 through a channel 7 in the lid 4 of the collection liner 3 and a channel 10 in the collection canister 1. The inlet for vacuum 13 comprises a hydrophobic filter 14.

The collection liner 3 is folded in such a manner that the lower volume of the lower part 41 of the collection liner 3 is folded inside the upper part 38 of the collection liner 3, i.e. the lower volume of the lower part 41 is upside down. Further, the first edge 34 of the collection liner 3 and the second edge 35 of the collection liner 3 are attached together by a joining strip 36 which may be an adhesive label, or any other suitable fastening means.

Figure 2:
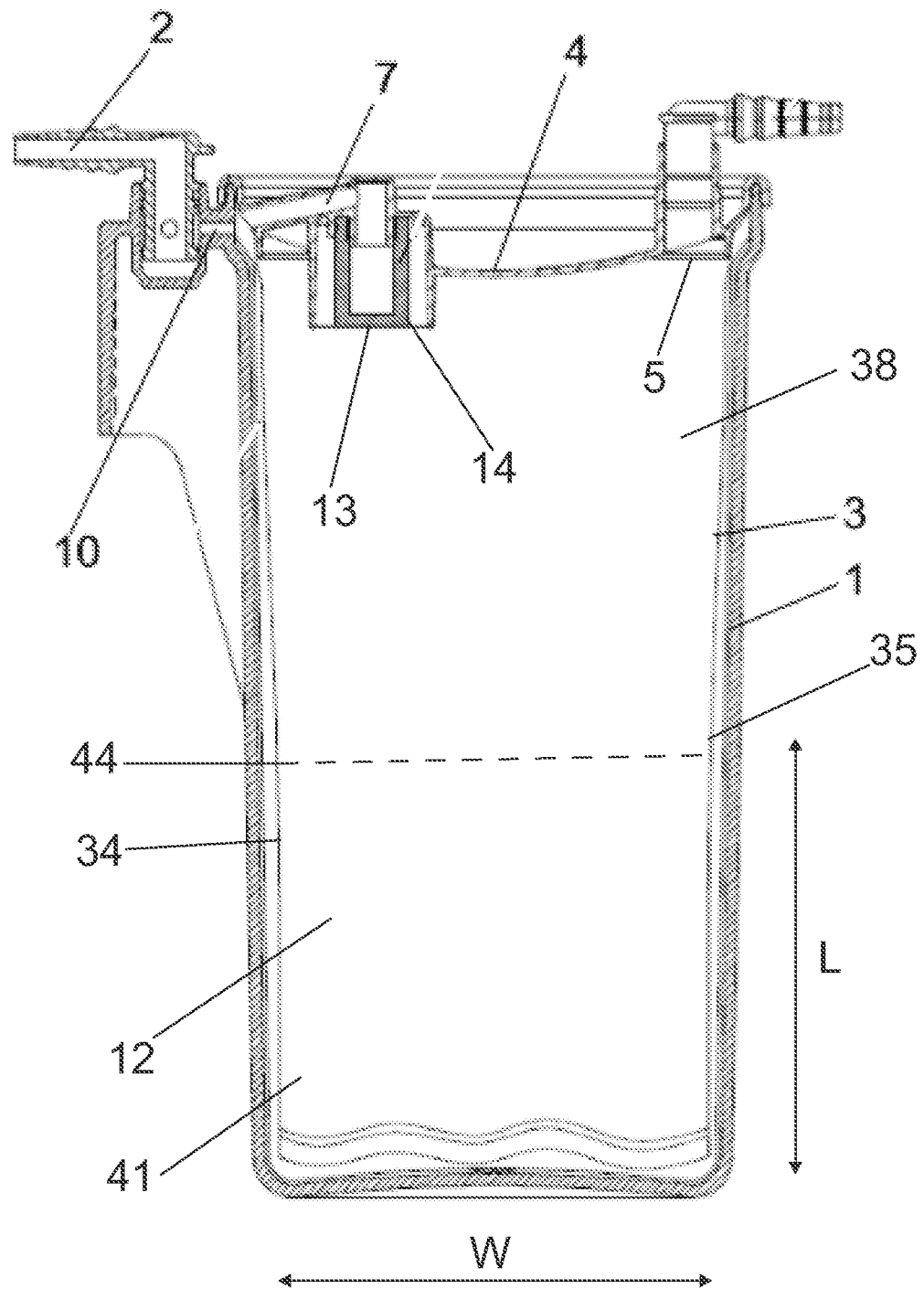
FIG. 2 shows a cross-sectional view of an unfolded collection liner with a lid inside a collection canister.

FIG. 2 shows a cross-sectional view of an unfolded collection liner 3 with a lid 4 inside a collection canister 1. The opening of the collection liner 3 is assisted by a pressure difference between the canister 1 and the collection liner 3. As the collection canister 1 is evacuated and air is led to the collection liner 3, the collection liner starts to inflate, and the joining strip 36, if it exists, breaks. The joining strip 36 usually breaks in two parts in such a manner that the parts stay attached to the bag portion and therefore, the collection canister remains clean. The joining strip 36 may be provided with a perforation which directs splitting of the joining strip 36.

The upper part 38 of the bag portion 12 spreads in such a manner that it comes into contact with the inner wall of the collection canister 1. The lower part 41 of the bag portion 12, which is folded inside the upper part of the bag portion, starts to roll out towards the bottom of the canister 1. Thus, the bag portion is reliably spread into the collection canister as shown in FIG. 2.

In practice, the collection liner 3 is put on the collection container 1 and vacuum is turned on. Then the centre of the lid 4 is pressed lightly and the collection liner 3 opens. When the collection liner is opened the collection tube is closed. Vacuum sucks the lid into its place onto the rim of the collection canister 1 and vacuum is turned off. The collection liner is ready for use.

Figure 3:
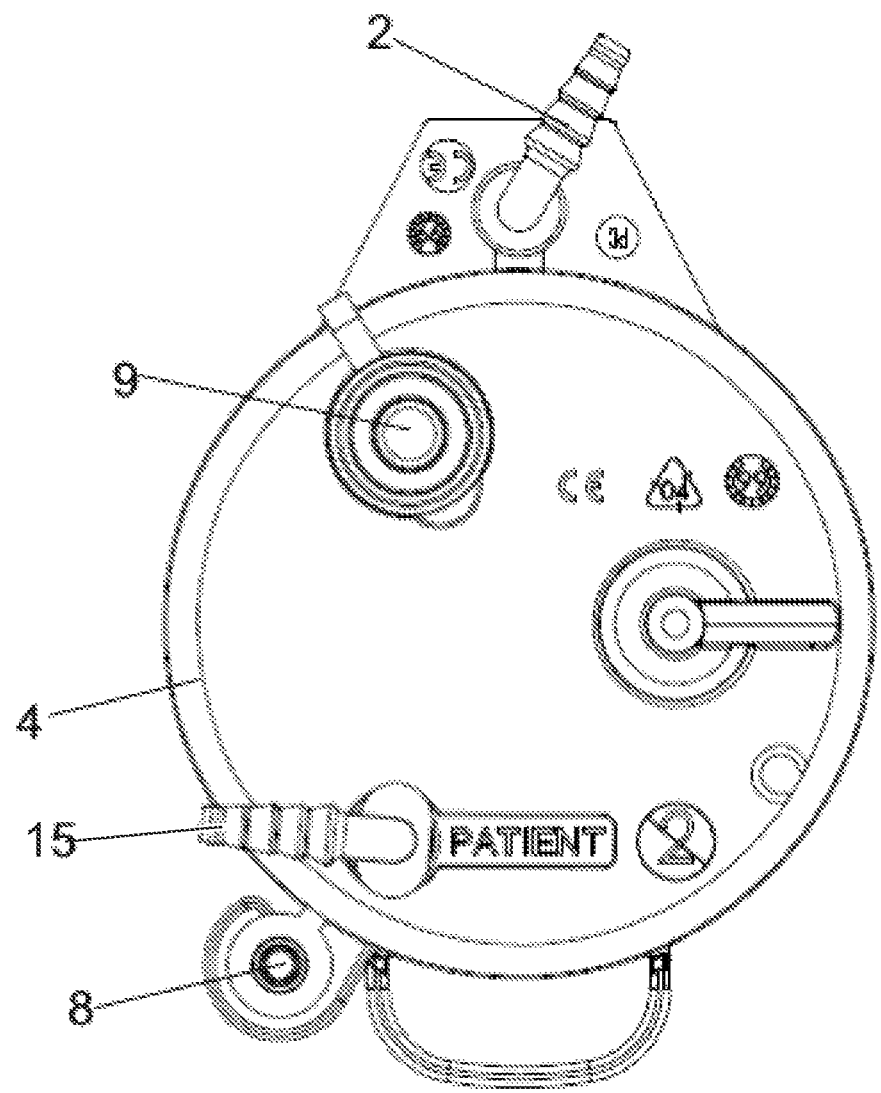
FIG. 3 shows a collection liner with a lid from above.

FIG. 3 is a top view of the collection liner arrangement. In addition to the parts disclosed with reference to FIGS. 1 and 2, FIG. 3 shows a plug 8 integrated in the lid 4 for closing the collection tube connector 15 after use, and a fitting 9 used for connecting collection liner arrangements in series, for taking samples and for emptying.

Figure 4:
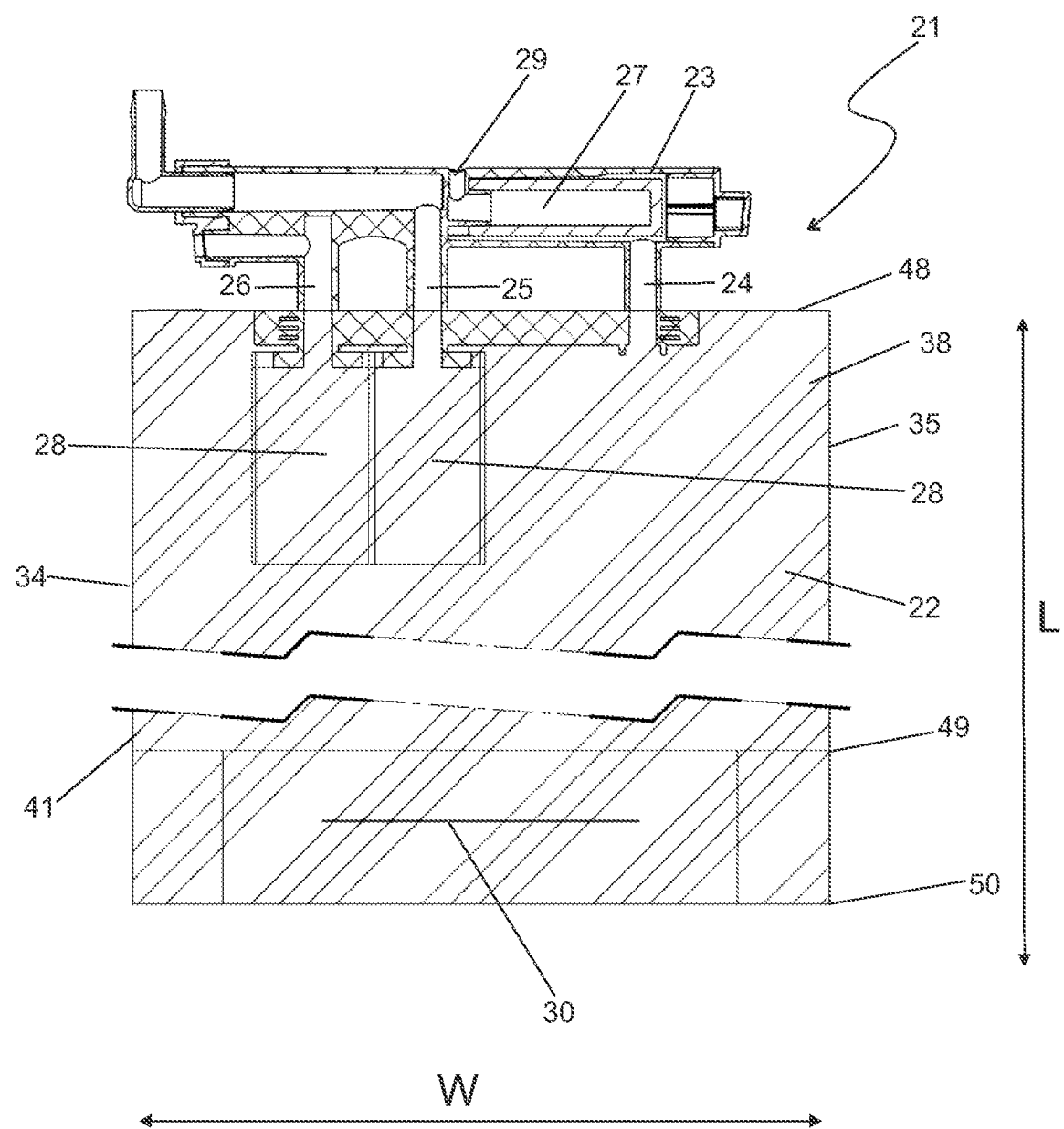
FIG. 4 shows a cross-sectional view of a collection liner with a handle.

FIG. 4 shows a collection liner 21 as a cross sectional view. The collection liner comprises a closed bag portion 22 made of a flexible plastic film and a handle 23. The handle 23 serves as a handy grip but there are also functional channels inside the handle 23. The bag portion 22 and the handle 23 are attached to each other in such a manner that inlets 24, 25, 26, which advance inside the handle 23, open into the bag portion but otherwise the bag portion 22 is closed by a seam 48. The inlet 24 is for vacuum. The vacuum is connected to the collection liner 21 through an opening 29. In the inlet 24 for the vacuum there is a hydrophobic filter 27. The inlet 25 is for a collection tube. The inlet 25 has a first end to which the collection tube is joined and a second end which opens to the bag portion 22. The inlet 26 is for a solidifying agent or any other chemical additive entering into the collection liner 21.

Each inlet 24, 25, 26 is provided with a back flow preventing means, i.e. a back flow preventing device. The inlet 24 for vacuum comprises a hydrophobic filter 27 which swells if liquid reaches it, thus closing the flow. The inlet 25 for the collection tube and the inlet 26 for the solidifying agent are surrounded with a thin plastic tube inside the bag portion 22. The thin plastic tube is fastened directly to the inlets. It forms a no-return valve 28. The no-return valve 28 is open only when the pressure inside the thin plastic tube is higher than around it. The thin plastic tube comprises two parallel films joined together e.g. by welding. This structure confirms that the plastic tube seals properly without openings in the edges.

There is an ancillary handle 30 at the bottom of the bag portion 22. The ancillary handle 30 may be a slit which is formed under a seam 49 which closes the bag portion 22. There may be another seam 50 which is parallel with the above-mentioned seam 49.

Figure 5:
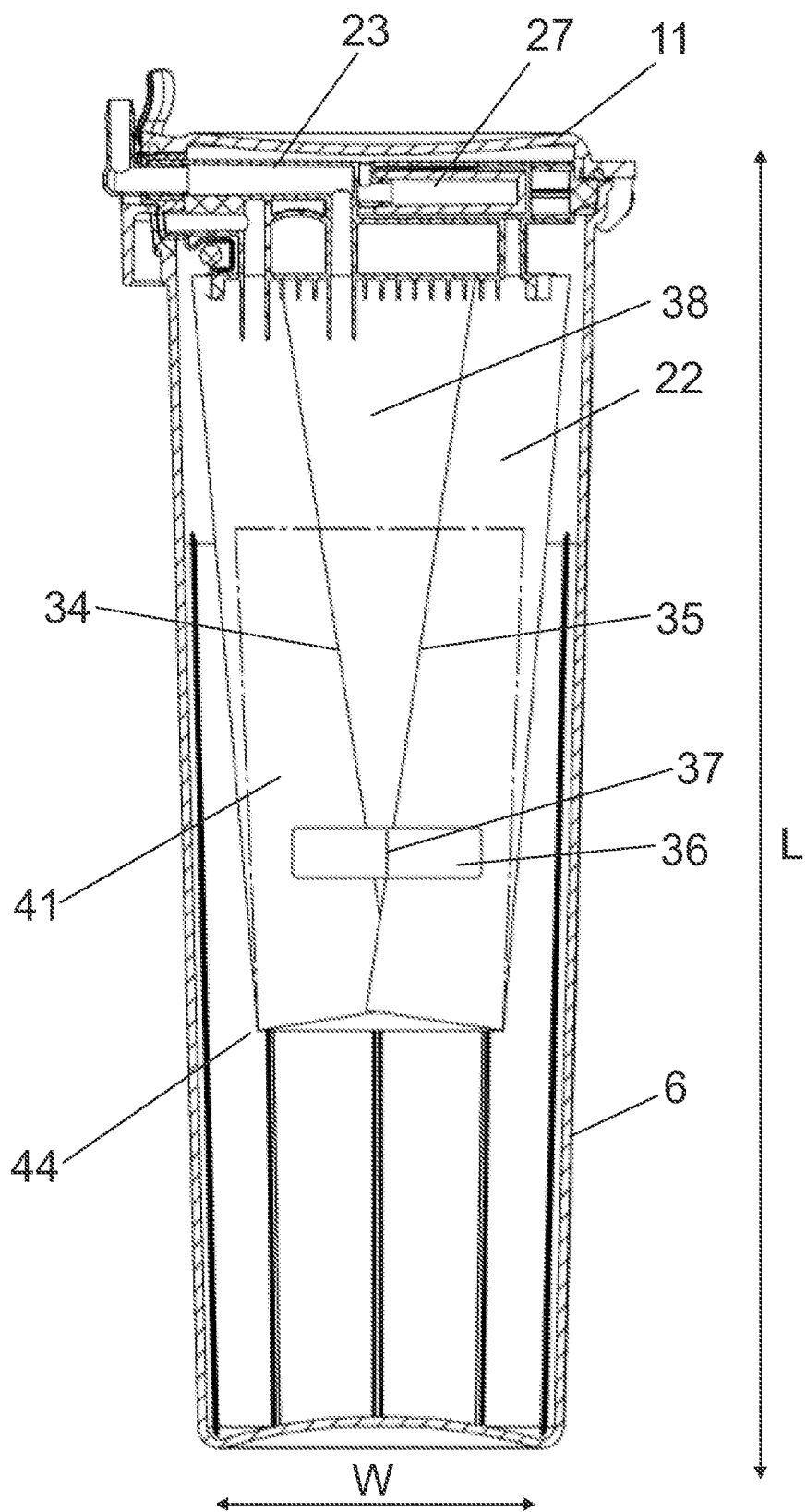
FIG. 5 shows a cross-sectional view of a folded collection liner with a handle inside a collection canister.

FIG. 5 shows a collection liner 21 inside a canister 6. The collection canister 6 is provided with a lid 11. The bag portion 22 is folded in such a manner that the lower part 41 of the bag portion is folded inside the upper portion 38 in such a manner that a fold 44 is formed.

The bag portion comprises a first edge 34 in the width direction and a second edge 35 in the width direction. The first edge 34 and the second edge 35 are attached together by a joining strip 36, such as a label. The joining strip 36 may comprise a perforation 37.

Figure 6:
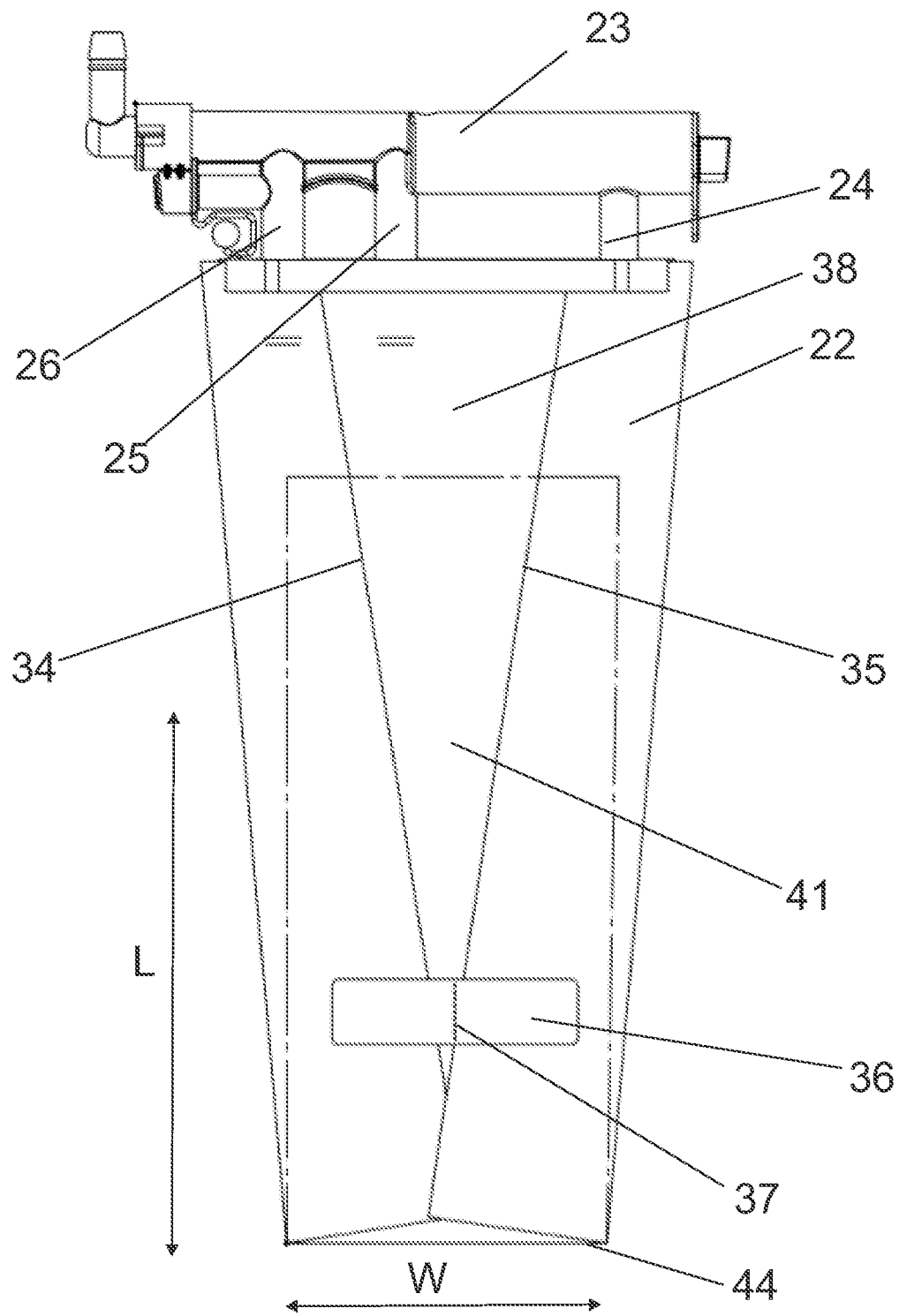
FIG. 6 shows a side view of a collection liner with a handle as folded.
Figure 7:
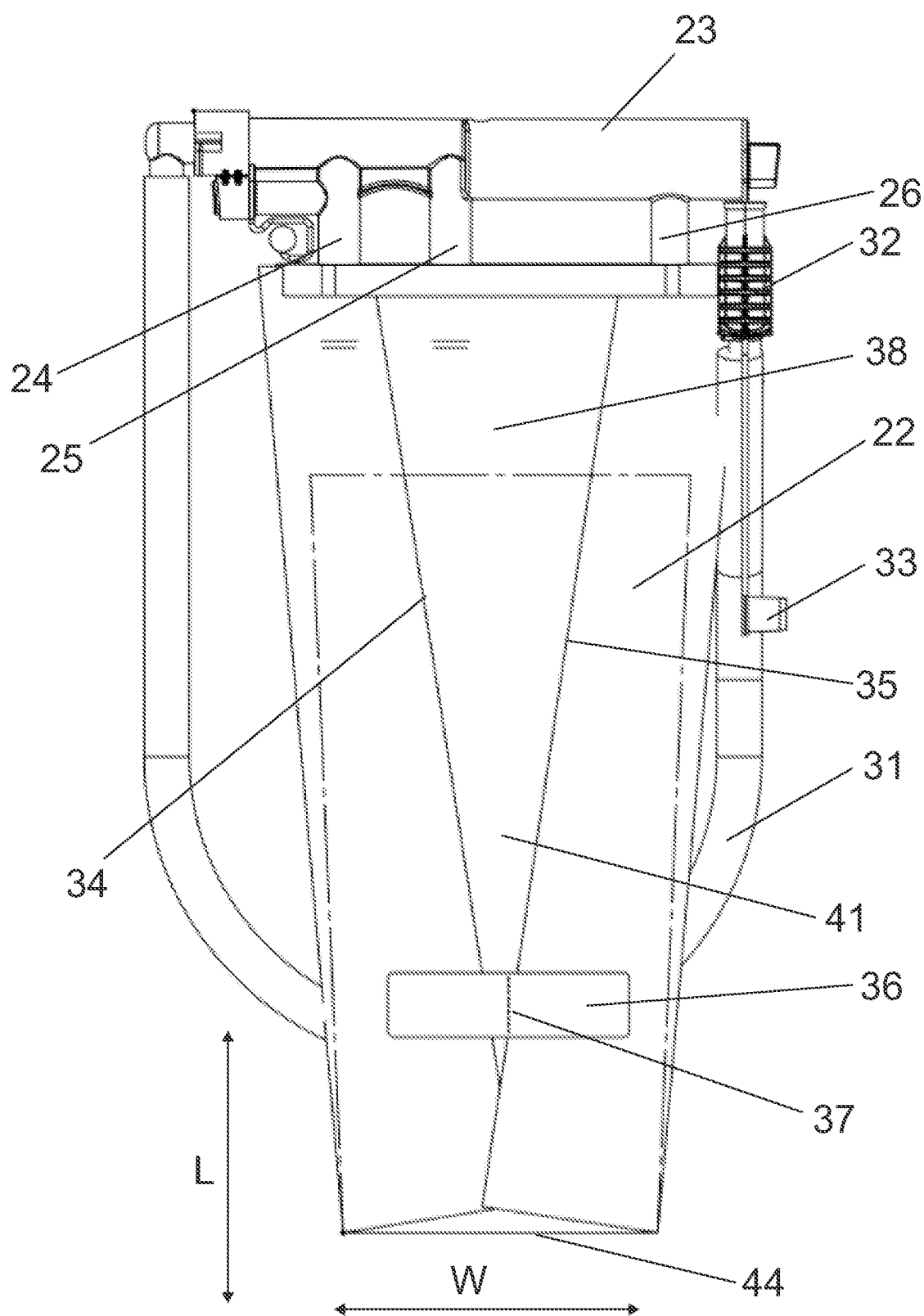
FIG. 7 shows a side view of a collection liner with a handle and a collection tube as folded.

FIGS. 6 and 7 show folded collection liners 21. The collection liner 21 in FIG. 7 is provided with a collection tube 31 with an adapter 32 provided with a cap 33.

Figure 8:
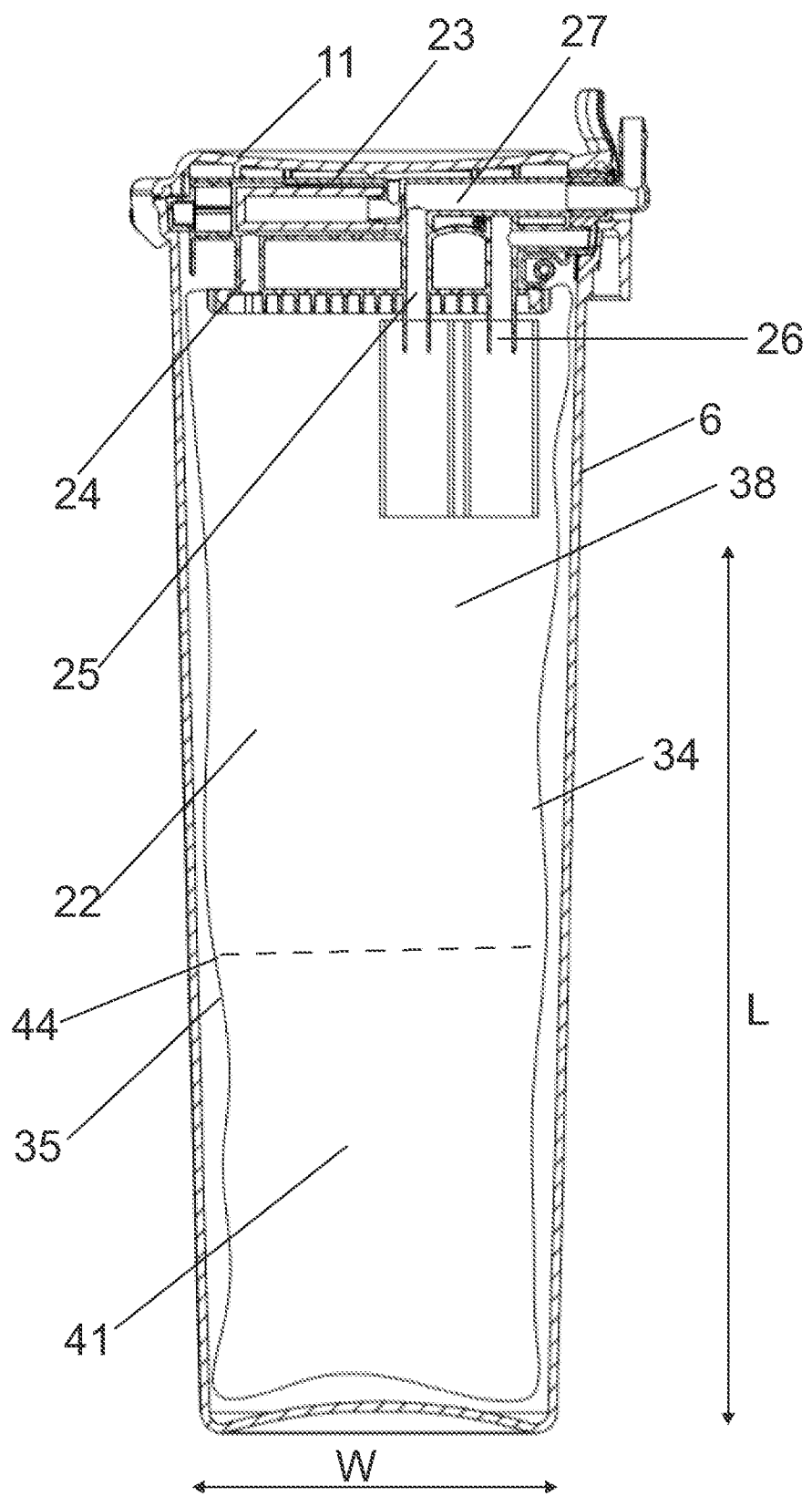
FIG. 8 shows a cross-sectional view of an unfolded collection liner inside a collection canister.

FIG. 8 shows the opened collection liner 21 inside the canister 6. The opening of the collection liner 21 is assisted by a pressure difference between the canister 6 and the collection liner 21. As the collection canister 6 is evacuated and air is led to the collection liner 21, the collection liner starts to inflate, and the joining strip 36, if it exists, breaks. The perforation 37 enhances breaking. The joining strip 36 usually breaks in two parts in such a manner that the parts stay attached to the bag portion and therefore, the collection canister remains clean. Thus, the upper part 38 of the bag portion 22 spreads in such a manner that it comes into contact with the inner wall of the canister 6. The lower volume of the lower part 41 of the bag portion 22, which is folded inside the upper part 38 of the bag portion 22, starts to roll out towards the bottom of the canister 6. The folded parts of the bag portion do not rub against each other and the bag portion has no chance to stick to the side wall of the canister. Thus, the bag portion is reliably spread into the collection canister.

In practice, the collection liner 21 is put into the collection canister 6. The lid 11 of the collection canister 6 is closed. The collection tube 31 is closed. The collection canister 6 is evacuated. The inner part of the collection liner 21 is connected to air via a suction port or via a solidifying port. Air starts to flow in to the collection liner and through the hydrophobic filter 27 from the collection liner 21 to the collection canister 6. The pressure difference between the collection canister and collection liner opens the collection liner 21 in such a manner that the upper part of the bag portion comes into contact with the inner wall of the collection canister 6.

After that the lower part rolls out towards the bottom of the collection canister 6. As the assembly of the collection liner 21 is completed, vacuum in the collection canister 6 is turned off and the contact with the ambient air is closed. The above-mentioned steps may be accomplished automatically by a suitable collection container arrangement.

It will be obvious to a person skilled in the art that, as the technology advances, the inventive concept can be implemented in various ways. The invention and its embodiments are not limited to the examples described above but may vary within the scope of the claims.

What is claimed is:

1. A collection liner for a medical or a surgical operation, the collection liner comprising a closed flexible bag portion, the closed flexible bag portion having a width direction and a length direction, and an upper part of the bag portion in the length direction and a lower part of the bag portion in the length direction, the lower part comprising a lower volume, wherein the lower part of the bag portion is folded inside the upper part of the bag portion in such a manner that the entire lower volume of the lower part is upside down inside the upper part prior to use, and wherein an inner surface of the lower part of the bag portion faces an inner surface of the upper part.

2. The collection liner according to claim 1, wherein there is a fold between the upper part of the bag portion and the lower part of the bag portion.

3. The collection liner according to claim 1, wherein the collection liner comprises a first edge in the width direction and a second edge in the width direction and the collection liner is folded in the width direction in such a manner that the first edge and the second edge are attached together by a joining strip.

4. The collection liner according to claim 3, wherein the joining strip is an adhesive label.

5. The collection liner according to claim 1, wherein the flexible bag portion is closed by a lid.

6. The collection liner according to claim 1, wherein the flexible bag portion is closed by a handle.

* * * * *